United States Patent
Miyamoto et al.

(10) Patent No.: US 10,457,632 B2
(45) Date of Patent: Oct. 29, 2019

(54) PRODUCTION METHOD FOR ISOCYANATE COMPOUND

(71) Applicant: SUMITOMO CHEMICAL COMPANY, LIMITED, Tokyo (JP)

(72) Inventors: Takashi Miyamoto, Oita (JP); Yuta Nagashima, Osaka (JP); Masaji Hirota, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/062,275

(22) PCT Filed: Dec. 14, 2016

(86) PCT No.: PCT/JP2016/087245
§ 371 (c)(1),
(2) Date: Jun. 14, 2018

(87) PCT Pub. No.: WO2017/104709
PCT Pub. Date: Jun. 22, 2017

(65) Prior Publication Data
US 2018/0354894 A1 Dec. 13, 2018

(30) Foreign Application Priority Data
Dec. 18, 2015 (JP) .................. 2015-247040

(51) Int. Cl.
*C07C 263/10* (2006.01)
*C07C 265/12* (2006.01)

(52) U.S. Cl.
CPC .......... *C07C 263/10* (2013.01); *C07C 265/12* (2013.01)

(58) Field of Classification Search
CPC .......................... C07C 263/10; C07C 265/12
USPC ....................................................... 560/347
See application file for complete search history.

(56) References Cited

U.S. PATENT DOCUMENTS

| 6,060,484 | A | 5/2000 | Fritz et al. |
| 9,565,856 | B2 | 2/2017 | Yoshimoto et al. |
| 2015/0051171 | A1* | 2/2015 | Yoshimoto ........... A01N 43/713 |
| 2016/0081339 | A1 | 3/2016 | Yoshimoto et al. |
| 2017/0342023 | A1 | 11/2017 | Yoshimoto et al. |

FOREIGN PATENT DOCUMENTS

| CN | 1687022 A | 10/2005 |
| CN | 1939899 A | 4/2007 |
| EP | 2 990 404 A1 | 3/2016 |
| JP | 2000-510833 A | 8/2000 |
| JP | 2014-80415 A | 5/2014 |
| WO | WO 2013/162072 A1 | 10/2013 |
| WO | WO 2014/175465 A1 | 10/2014 |
| WO | WO 2016/098561 A1 | 6/2016 |

OTHER PUBLICATIONS

Cantagrel et al., "Iron Trichloride-Promoted Cyclization of o-Alkynylaryl Isocyanates: Synthesis of 3-(Chloromethylene)oxindoles," Organic Letters, vol. 11, No. 19, 2009 (published online Sep. 9, 2009), pp. 4262-4265.
International Preliminary Report on Patentability and English translation of the Written Opinion of the International Searching Authority (Forms PCT/IB/373 and PCT/ISA/237) for International Application No. PCT/JP2016/087245, dated Jun. 19, 2018.
International Search Report (Form PCT/ISA/210) for International Application No. PCT/JP2016/087245, dated Jan. 24, 2017.
European Patent Office Communication and extended search report issued in the corresponding European Patent Application No. 16875686.4 dated Apr. 12, 2019.

* cited by examiner

*Primary Examiner* — Deborah D Carr
(74) *Attorney, Agent, or Firm* — Birch, Stewart, Kolasch & Birch, LLP

(57) ABSTRACT

The present invention provides a process for producing an isocyanate compound such as 3-methyl-2-methoxymethyl-1-isocyanate benzene and the like. By reacting 3-Methyl-2-methoxymethyl aniline and the like with phosgene in the presence of a tertiary amine at 10° C. to 14° C. in one or more solvents selected from the group consisting of toluene and xylene, isocyanate compounds such as 3-methyl-2-methoxymethyl-1-isocyanate benzene and the like can be produced at high yield.

5 Claims, No Drawings

PRODUCTION METHOD FOR ISOCYANATE COMPOUND

TECHNICAL FIELD

The present invention relates to a process for producing an isocyanate compound.

BACKGROUND ART

A compound represented by formula (2) (hereinafter, sometimes referred to as Compound (2)):

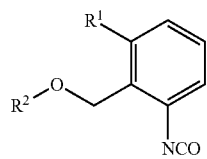

(2)

wherein $R^1$ represents a methyl group, a cyclopropyl group, a chlorine atom, a bromine atom, an ethyl group, or a methoxy group, and $R^2$ represents an alkyl group having one to six carbon atoms, is useful as an intermediate compound for agrochemicals (see Patent Document 1), and Reference Production Example 18 of the Patent document 1 describes that a mixture of 3-methyl-2-methoxymethylaniline, triphosgene, saturated aqueous sodium bicarbonate solution, and ethyl acetate was stirred under ice-cooling to produce 3-methyl-2-methoxymethyl-1-isocyanate benzene.

CITATION LIST

Patent Document

Patent Document 1: WO 2013/162072

SUMMARY OF THE INVENTION

Problems to be Solved by Invention

However, the process described in Patent Document 1 is not an industrially sufficient process in terms of yield. The object of the present invention is to provide a process for producing isocyanate compounds such as 3-methyl-2-methoxymethyl-1-isocyanate benzene and the like at higher yield.

Means to Solve Problems

The present inventors have studied the above-mentioned problems, and found out the following process.
That is, the present invention is as follows.
[1] A process for producing an isocyanate compound represented by formula (2):

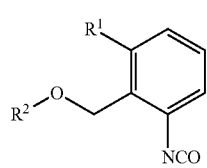

(2)

wherein $R^1$ represents a methyl group, a cyclopropyl group, a chlorine atom, a bromine atom, an ethyl group, or a methoxy group, and $R^2$ represents an alkyl group having one to six carbon atoms, which comprises reacting a compound represented by formula (1):

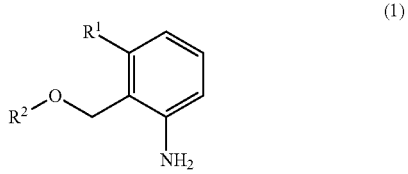

(1)

wherein $R^1$ and $R^2$ are the same as defined above, with phosgene in the presence of a tertiary amine at 9° C. to 16° C. in one or more solvents selected from the group consisting of toluene and xylene.
[2] The process according to [1] wherein the reaction is carried out at 10° C. to 14° C.
[3] The process according to [1] or [2] wherein $R^1$ represents a methyl group and $R^2$ represents a methyl group.
[4] The process according to any one of [1] to [3] wherein the tertiary amine is triethylamine.
[5] The process according to any one of [1] to [4] wherein the solvent is toluene.

Effect of the Invention

According to the prevent invention, isocyanate compounds such as 3-methyl-2-methoxymethyl-1-isocyanate benzene and the like can be produced at high yield.

MODE FOR CARRYING OUT THE INVENTION

The process for producing an isocyanate compound represented by formula (2) is described.
The isocyanate compound represented by formula (2) can be produced by reacting a compound represented by formula (1) (hereinafter, sometimes referred to as Compound (1)):

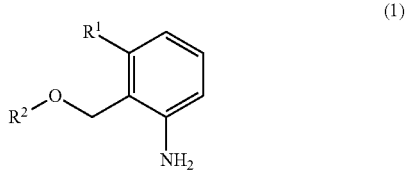

(1)

wherein $R^1$ and $R^2$ are the same as defined above, with phosgene in the presence of a tertiary amine at 9° C. to 16° C. in one or more solvents selected from the group consisting of toluene and xylene.
Examples of an alkyl group having one to six carbon atoms as $R^2$ group include methyl group, ethyl group, propyl group, isopropyl group, butyl group, sec-butyl group, tert-butyl group, pentyl group, and hexyl group. The preferable alkyl group having one to six carbon atoms as $R^2$ group is methyl group and ethyl group.
The solvent to be used in the reaction is toluene, xylene or mixtures thereof, and preferably toluene. The use amount of the solvents is usually 3 to 20 times by weight relative to the compound (1).

The use amount of phosgene is usually 0.95 to 1.5 moles, preferably 1.0 to 1.3 moles, relative to 1 mole of the compound (1).

Examples of the tertiary amine to be used in the reaction include triethylamine, diisopropylethylamine, N-methylmorpholine, N-methylpiperidine, diazabicycloundecene, and the like. The tertiary amine is preferably trialkylamine such as triethylamine and diisopropylethylamine, more preferably triethylamine.

The use amount of the tertiary amine is usually 1.8 to 3.0 moles, preferably 2.0 to 2.6 moles, relative to 1 mole of the phosgene.

The reaction temperature is 9° C. to 16° C., preferably 10° C. to 14° C.

In the reaction, the order of mixing the compound (1), the phosgene, and the tertiary amine is preferably adding the compound (1) to solvent and the phosgene, followed by an addition of the tertiary amine. Each of the reactant compounds is preferably added dropwise in portionwise thereof in terms of the yield. Though the time of dropwise addition of each of the reactant compounds depends on the amounts thereof, it is usually 30 minutes to 24 hours. Preferably, the compound (1) is added dropwise over 2 to 24 hours, and the tertiary amine is added dropwise over 4 to 24 hours.

After the completion of the dropwise addition of each of the reactant compounds, the reaction mixtures are usually stirred at 10° C. to 14° C. for 0.1 to 6 hours.

After the completion of the reaction, the compound (2) can be isolated by carrying out a post-treatment procedure such as filtration of the reaction mixture. The compound (2) may be purified by further procedures such as distillation and chromatography.

EXAMPLES

Example 1

Under nitrogen atmosphere, 382.0 g of Toluene was cooled to 10° C. At the same temperature, a dropwise addition of 78.6 g of 3-methyl-2-methoxymethylaniline and a bubbling of 61.7 g of phosgene were carried out concurrently over 3 hours, and after the completion of the procedures, the reaction mixture was stirred at the same temperature for 1.5 hours. A mixture of 126.3 g of triethylamine and 78.6 g of toluene was added dropwise to the resulting mixture over 5 hours, and the mixture was stirred for 3 hours to precipitate out crystals. The obtained crystals were filtered, and a filtrate was analyzed with liquid chromatography to find that 88.8 g of 3-methyl-2-methoxymethyl-1-isocyanate benzene was contained in the filtrate (yield 96.4%).

Example 2

Under nitrogen atmosphere, 254.6 g of toluene was cooled to 12° C. At the same temperature, a dropwise addition of 52.4 g of 3-methyl-2-methoxymethylaniline and a bubbling of 41.2 g of phosgene were carried out concurrently over 3 hours, and after the completion of the procedures, the reaction mixture was stirred at the same temperature for 1.5 hours. A mixture of 94.7 g of triethylamine and 52.4 g of toluene was added dropwise to the resulting mixture over 5 hours, and the mixture was stirred for 3 hours to precipitate out crystals. The obtained crystals were filtered, and a filtrate was analyzed with liquid chromatography to find that 59.5 g of 3-methyl-2-methoxymethyl-1-isocyanate benzene was contained in the filtrate (yield 96.8%).

Example 3

Under nitrogen atmosphere, 254.6 g of toluene was cooled to 14° C. At the same temperature, a dropwise addition of 52.4 g of 3-methyl-2-methoxymethylaniline and a bubbling of 41.2 g of phosgene were carried out concurrently over 3 hours, and after the completion of the procedures, the reaction mixture was stirred at the same temperature for 1.5 hours. A mixture of 94.7 g of triethylamine and 52.4 g of toluene was added dropwise to the resulting mixture over 5 hours, and the mixture was stirred for 3 hours to precipitate out crystals. The obtained crystals were filtered, and a filtrate was analyzed with liquid chromatography to find that 59.9 g of 3-methyl-2-methoxymethyl-1-isocyanate benzene was contained in the filtrate (yield 97.4%).

Example 4

Under nitrogen atmosphere, 382.0 g of toluene was cooled to 9° C. At the same temperature, a dropwise addition of 78.6 g of 3-methyl-2-methoxymethylaniline and a bubbling of 61.7 g of phosgene were carried out concurrently over 3 hours, and after the completion of the procedures, the reaction mixture was stirred at the same temperature for 1.5 hours. A mixture of 126.3 g of triethylamine and 78.6 g of toluene was added dropwise to the resulting mixture over 5 hours, and the mixture was stirred for 3 hours to precipitate out crystals. The obtained crystals were filtered, and a filtrate was analyzed with liquid chromatography to find that 92.1 g of 3-methyl-2-methoxymethyl-1-isocyanate benzene was contained in the filtrate (yield 93.1%).

Example 5

Under nitrogen atmosphere, 254.6 g of toluene was cooled to 15° C. At the same temperature, a dropwise addition of 52.4 g of 3-methyl-2-methoxymethylaniline and a bubbling of 41.2 g of phosgene were carried out concurrently over 3 hours, and after the completion of the procedures, the reaction mixture was stirred at the same temperature for 1.5 hours. A mixture of 94.7 g of triethylamine and 52.4 g of toluene was added dropwise to the resulting mixture over 5 hours, and the mixture was stirred for 3 hours to precipitate out crystals. The obtained crystals were filtered, and a filtrate was analyzed with liquid chromatography to find that 57.9 g of 3-methyl-2-methoxymethyl-1-isocyanate benzene was contained in the filtrate (yield 94.3%).

Example 6

Under nitrogen atmosphere, 254.6 g of toluene was cooled to 16° C. At the same temperature, a dropwise addition of 52.4 g of 3-methyl-2-methoxymethylaniline and a bubbling of 41.2 g of phosgene were carried out concurrently over 3 hours, and after the completion of the procedures, the reaction mixture was stirred at the same temperature for 1.5 hours. A mixture of 94.7 g of triethylamine and 52.4 g of toluene was added dropwise to the resulting mixtures over 5 hours, and the mixture was stirred for 3 hours to precipitate out crystals. The obtained crystals were filtered, and a filtrate was analyzed with liquid chromatography to find that 57.1 g of 3-methyl-2-methoxymethyl-1-isocyanate benzene was contained in the filtrate (yield 92.9%).

Example 7

Under nitrogen atmosphere, 254.6 g of xylene was cooled to 12° C. At the same temperature, a dropwise addition of 52.4 g of 3-methyl-2-methoxymethylaniline and a bubbling of 41.2 g of phosgene were carried out concurrently over 3 hours, and after the completion of the procedures, the reaction mixture was stirred at the same temperature for 1.5 hours. A mixture of 94.7 g of triethylamine and 52.4 g of xylene was added dropwise to the resulting mixture over 5 hours, and the mixture was stirred for 3 hours to precipitate out crystals. The obtained crystals were filtered, and a filtrate was analyzed with liquid chromatography to find that 58.9 g of 3-methyl-2-methoxymethyl-1-isocyanate benzene was contained in the filtrate (yield 95.9%).

Reference Examples

Under nitrogen atmosphere, 254.6 g of toluene was cooled to each of the temperatures shown in the Table below. At the same temperature, a dropwise addition of 52.4 g of 3-methyl-2-methoxyaniline and a bubbling of 41.2 g of phosgene were carried out concurrently over 3 hours, and after the completion of the procedures, the reaction mixture was stirred at the same temperature for 1.5 hours. A mixture of 94.7 g of triethylamine and 52.4 g of toluene was added dropwise to the resulting mixture over 5 hours, and the mixture was stirred for 3 hours to precipitate out crystals. The obtained crystals were filtered and a filtrate was analyzed with liquid chromatography to find that 3-methyl-2-methoxymethyl-1-isocyanate benzene was obtained at each of the yields shown in the Table 1 below.

TABLE 1

|  | Reference Example 1 | Reference Example 2 |
| --- | --- | --- |
| Reaction temperature | 8° C. | 20° C. |
| Yield | 85.2% | 67.0% |

INDUSTRIAL APPLICABILITY

According to the present invention, isocyanate compounds such as 3-methyl-2-methoxymethyl-1-isocyanate benzene and the like can be produced.

The invention claimed is:

1. A process for producing an isocyanate compound of formula (2):

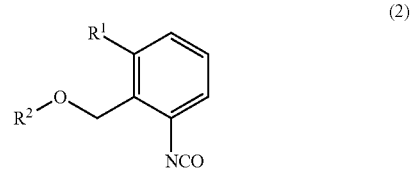

wherein $R^1$ represents a methyl group, a cyclopropyl group, a chlorine atom, a bromine atom, an ethyl group, or a methoxy group, and $R^2$ represents an alkyl group having one to six carbon atoms, which comprises reacting a compound of formula (1):

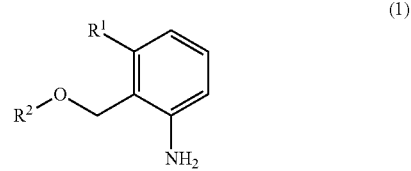

wherein $R^1$ and $R^2$ are the same as defined above, with phosgene in the presence of a tertiary amine at 9° C. to 16° C. in one or more solvents selected from the group consisting of toluene and xylene.

2. The process according to claim 1 wherein the reaction is carried out at 10° C. to 14° C.

3. The process according to claim 1 wherein $R^1$ represents a methyl group and $R^2$ represents a methyl group.

4. The process according to claim 1 wherein the tertiary amine is triethylamine.

5. The process according to claim 1 wherein the solvent is toluene.

* * * * *